United States Patent [19]
Yuichi et al.

[11] Patent Number: 5,519,188
[45] Date of Patent: May 21, 1996

[54] INCUBATOR

[75] Inventors: Tamaoki Yuichi; Sadami Hagiguchi; Kenji Nojima; Tetsuya Miyoshi, all of Gunma, Japan

[73] Assignee: Sanyo Electric Co., Ltd., Osaka, Japan

[21] Appl. No.: 277,885

[22] Filed: Jul. 20, 1994

[30] Foreign Application Priority Data

Jul. 22, 1993 [JP] Japan .................................. 5-201809

[51] Int. Cl.6 .......................... F27D 11/00; A01K 41/04
[52] U.S. Cl. ...................... 219/407; 219/398; 219/401; 236/3
[58] Field of Search .................... 219/385, 386, 219/387, 395, 398, 400, 401, 407; 236/2, 3

[56] References Cited

U.S. PATENT DOCUMENTS

| | | | |
|---|---|---|---|
| 4,572,427 | 2/1986 | Selfridge et al. | 236/3 |
| 4,923,816 | 5/1990 | Heeg et al. | 435/284 |
| 5,090,617 | 2/1992 | Swan et al. | 236/3 |

FOREIGN PATENT DOCUMENTS 2-13727  1/1990  Japan .................................. 219/407

Primary Examiner—Teresa J. Walberg
Assistant Examiner—J. Pelham
Attorney, Agent, or Firm—Darby & Darby

[57] ABSTRACT

An object of the present invention is to provide an incubator with improved control performance for the temperature and humidity in an inner box. The present invention is an incubator comprising an outer box having an inner portion made from a heat insulating material, an inner box disposed in the outer box through a space defined between the inner portion of the outer box and the inner box, a heating unit disposed in the space and adapted for heating the inside of the inner box, the heating unit being constructed of a plurality of heating means disposed at least on a bottom wall and left and right side walls of the inner box, and a control unit for independently controlling each of the heating means.

1 Claim, 4 Drawing Sheets

INCUBATOR

BACKGROUND OF THE INVENTION

1. Field of the Invention

The present invention relates to an incubator for use in scientific and chemical experiments for incubating bacteria and viruses.

2. Description of the Related Art

An incubator is disclosed in, for example, Japanese Patent Laid-Open Publication No. 3-17121 as a thermostatic cabinet. This thermostatic cabinet comprises a heat insulating box, a storage chamber, a heat insulating outer door, a heat insulating inner door, and a heater. The storage chamber is formed inside the heat insulating box. The outer door and inner door are used to open and close the opening of the storage chamber. The heater is buried in an inner bottom portion of the heat insulating box. The space is formed as a water storage layer. When the heater operates, water in the water storage layer is heated. The inside of the storage chamber is equally heated through the water storage layer. The space between the inner box and the heat insulating box may be an air layer through which the storage chamber is indirectly heated.

The inner box is indirectly heated so that the storage chamber is prevented from being dried. When incubating experiments for bacteria and viruses are performed, high humidity of approximately 98% RH is required. Thus, in such a thermostatic cabinet, a humidifying tray filled with water is disposed on the bottom of the storage chamber. Water is evaporated from the humidifying tray to keep the storage chamber at high humidity.

To keep the temperature in the thermostatic cabinet more equal, heaters should be disposed on, for example, left and right side portions of the heat insulating box as well as its bottom. However, conventionally, the heaters are connected in parallel to an electric circuit that controls their heat generation. In the case that the humidifying tray is disposed on the bottom of the storage chamber, if the temperature and humidity of the storage chamber are lowered due to the opening of the doors, the storage chamber is heated by heat generation (or increase of heat generation) of the heaters. However, before steam is sufficiently produced by the humidifying tray, the temperature of the storage chamber reaches a preset temperature. Thus, the heat generation or the increase of the heat generation by the heaters may be stopped. In this control system, the heat generation of the heater disposed on the insulating box bottom, which directly heats the humidifying tray, is stopped or decreased. Thus, after the doors are opened and closed, the increase of humidity in the storage chamber is delayed, thereby adversely affecting bacteria in the storage chamber.

Even if temperature sensors are disposed at various positions of the storage chamber, since the heat generation of the heaters are controlled in the same manner, the temperature in the storage chamber cannot be precisely controlled.

In addition, in the conventional incubating cabinet, since heaters are mounted to the walls of the heat insulating box and the inner box is heated through the water storage layer or the air layer, heat leaks out from the heat insulating box. Moreover, after the doors are opened and then closed, it takes a long time to restore the preset temperature of the incubating cabinet. During this time, the temperature in the incubating cabinet is unstable.

SUMMARY OF THE INVENTION

An object of the present invention is to provide an incubator with improved control performance of the temperature and humidity in an inner box thereof.

A first aspect of the present invention is a calculating apparatus, comprising an outer box having an inner portion made from a heat insulating material, an inner box disposed in the outer box through a space defined between the inner portion of the outer box and the inner box, a heating unit disposed in the space and adapted for heating the inside of the inner box. The heating unit is constructed of a plurality of heating means disposed at least on a bottom wall and left and right side walls of the inner box, and there is a control unit for independently controlling each of the heating means.

A second aspect of the present invention is an incubator, comprising an outer box having an inner portion made from a heat insulating material, an inner box disposed in the outer box through a space defined between the inner portion of the outer box and the inner box, and a heating unit disposed in the space and adapted for heating the inside of the inner box, with the heating unit being disposed in contact with the inner box.

These and other objects, features and advantages of the present invention will become more apparent in light of the following detailed description of a best mode embodiment thereof, as illustrated in the accompanying drawings.

DETAILED DESCRIPTION OF THE PREFERRED EMBODIMENT

Next, with reference to FIGS. 1 to 4, an embodiment of the present invention will be described.

Figure 1:
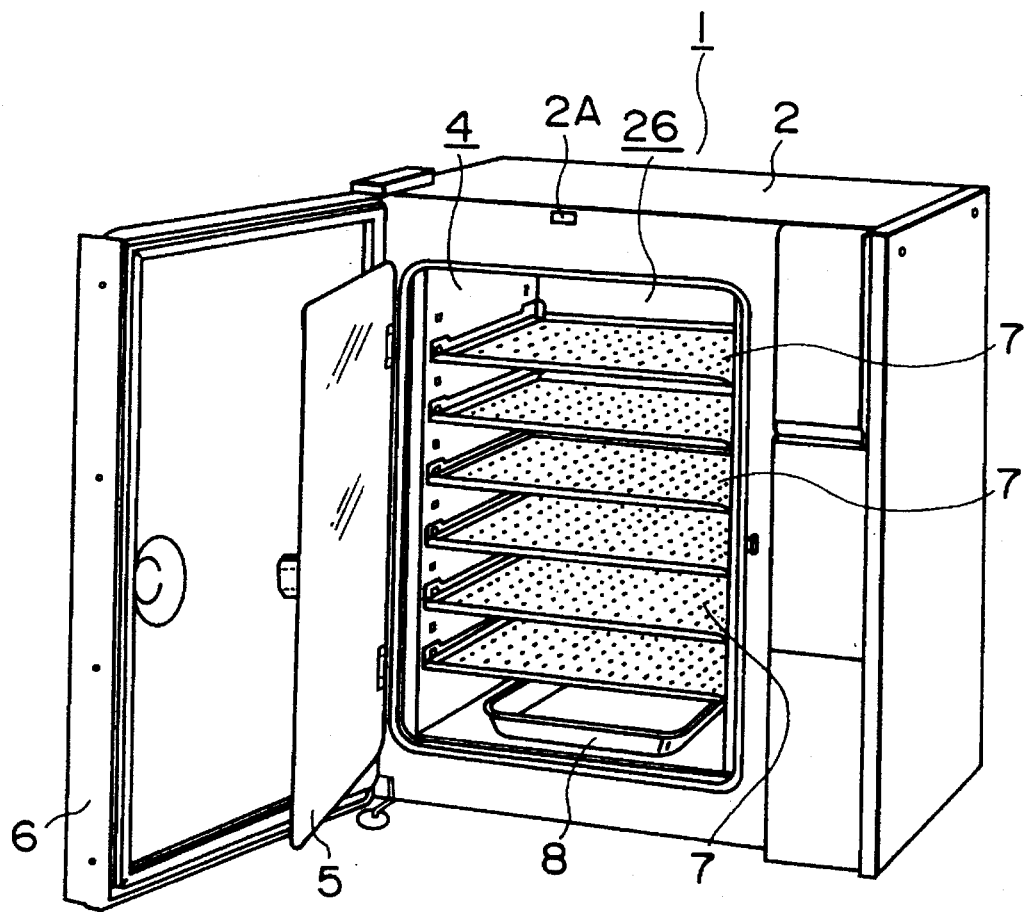
FIG. 1 is a perspective view showing an incubating cabinet as an embodiment of an incubator according to the present invention.
Figure 2:
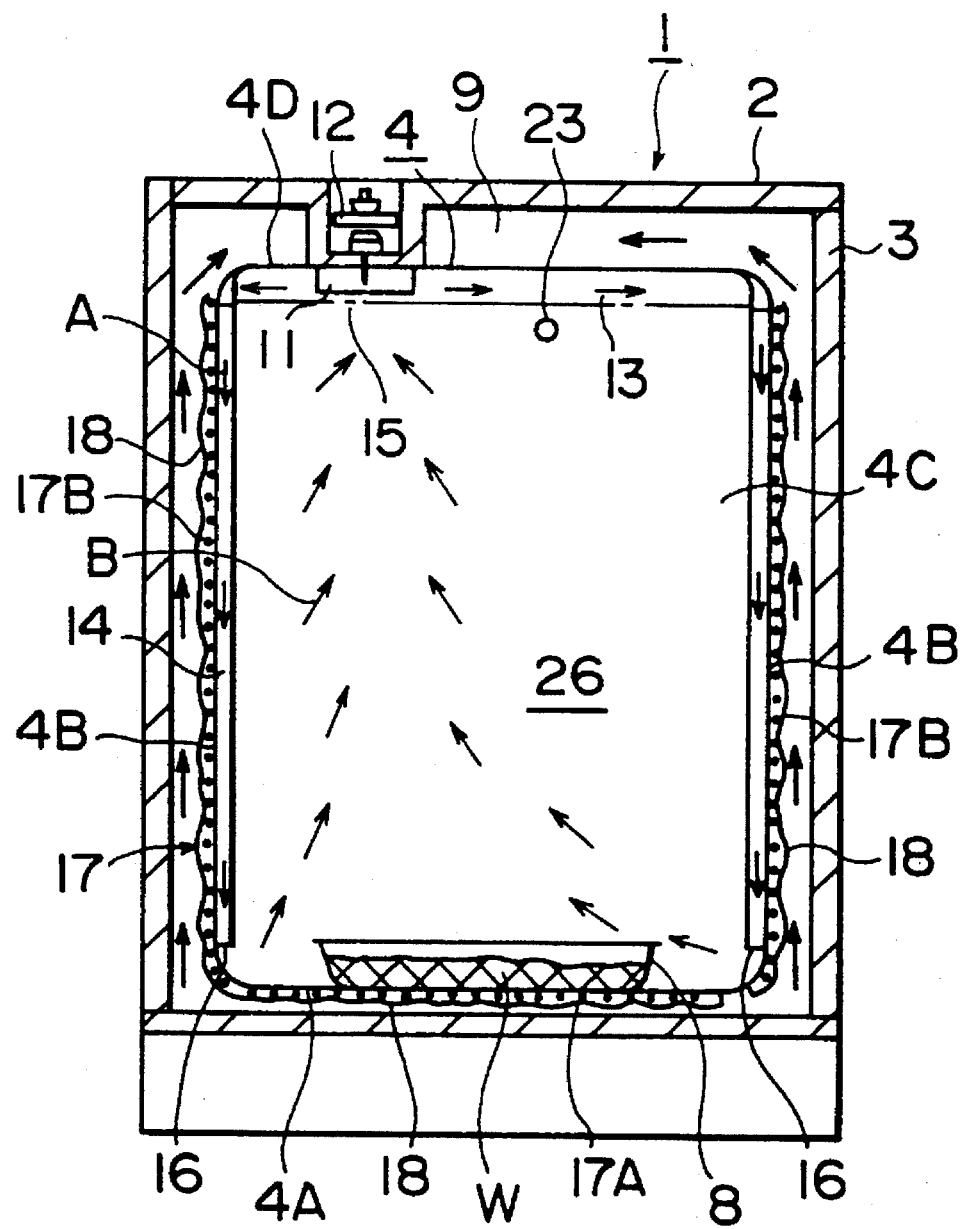
FIG. 2 is a vertical sectional front view showing the incubating cabinet.

In FIGS. 1 and 2, reference numeral 1 is a incubating cabinet 1 as an incubator according to the present invention. A heat insulating material 3 is disposed inside an outer box 2 of the incubating cabinet 1. An inner box 4 is disposed inside the heat insulating material 3 leaving a predetermined space 9 relative to the inner surface of the outer box. A storage chamber 26 is formed inside the inner box 4. The inner box 4 is composed of an anti-corrosive material such as stainless steel. The inner box 4 is constructed with a bottom wall 4A, left and right side walls 4B, 4B, a rear wall 4C, and a ceiling wall 4D. The front surface of the inner box 4 is open.

The front surface of the outer box 2 is open. The outer box 2 is closed and opened by a hinged heat insulating door 6. An inner door 5 is disposed inside the outer door 6. The front opening of the storage chamber 26 is opened and closed by the inner door 5. The inner door 5 is made of transparent glass. Thus, by opening the heat insulating outer door 6, the inside of the storage chamber 26 can be observed through the inner door 5. A door switch 2A is disposed on the outer box 2. The door switch 2A is turned on and off when the heat insulating outer door 6 is opened and closed, respectively. A temperature sensor 23 is disposed at an upper portion of the storage chamber 26. The temperature sensor is, for example, a thermistor.

A plurality of stages of shelves 7, . . . , 7 are disposed in the storage chamber 26. A humidifying tray 8 is disposed on the bottom wall 4A of the inner box 4. The upper surface of the humidifying tray 8 is open. When water W becomes empty in the humidifying tray 8, the tray 8 is removed from the storage chamber 26 and the water W is replenished.

A cabinet circulation fan 11 is disposed on a motor 12. The motor 12 rotates the fan 11. The motor 12 is disposed on the ceiling wall 4D of the inner box 4. The cabinet circulation fan 11 circulates air in the storage chamber 26. The motor 12 is insulated from the space 9 by the heat insulating material 3. A ceiling duct 13 and side ducts 14, 14 are disposed in the inner box 4. The cabinet circulation fan 11 is disposed in the ceiling duct 13. An air exhaust opening 15 is disposed adjacent to the cabinet circulation fan 11 of the ceiling duct 13. Air blowing openings 16, 16 are disposed below the side ducts 14, 14.

A heater 17 that is a heating unit is disposed outside the inner box 4. The heater 17 is constructed of a bottom heater 17A, side heaters 17B, 17B, and a rear heater 17C that are disposed in contact with the bottom wall 4A, the left and right side walls 4B, 4B, and the rear wall 4C, respectively. The heaters 17A, 17B, 17B, and 17C are adhered to the outer surfaces of the inner wall 4 by an aluminum tape 18. However, the heaters 17A, 17B, 17B, and 17C may be adhered to the outer surfaces of the inner box 4 by heat resisting adhesive agent or fasteners (not shown).

Figure 3:
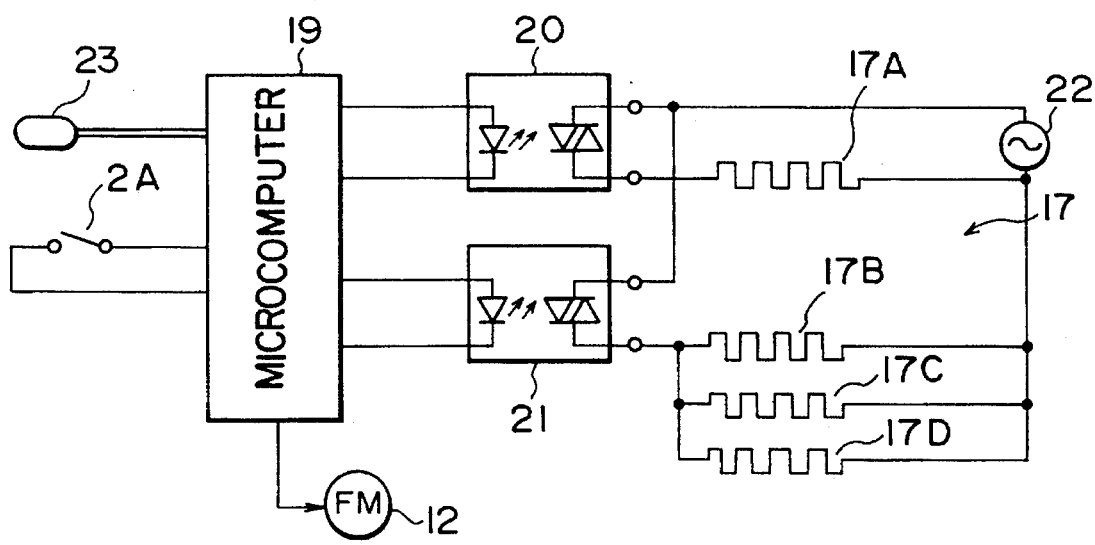
FIG. 3 is a schematic diagram showing an electric circuit of the incubating cabinet as the embodiment of the incubator according to the present invention.

FIG. 3 shows an electric circuit of a control unit 19. The control unit 19 is constructed of a general purpose microcomputer. Output signals of the door switch 2A and the temperature sensor 23 are input to the control unit 19. Outputs of the control unit 19 are connected to control switches 20 and 21. The control switches 20 and 21 are constructed of photocouplers. Another output of the control unit 19 is connected to the motor 12. The bottom heater 17A is connected to an AC power supply 22 through the control switch 20. The side heaters 17B, 17B, the rear heater 17C, and the door heater 17D of the heat resisting outer door 6 are connected in parallel, thereby forming a parallel circuit. The parallel circuit is connected to the AC power supply 22 through the control switch 21.

Thus, the control system of the bottom heater 17A for the bottom wall 4A is different from the control system of the side heaters 17B, 17B for the left and right side walls 4B, 4B, the rear heater 17C for the rear wall 4C, and the door heater 17D. The control unit 19 performs PID control or the like so as to turn on and off the switches 20 and 21 corresponding to a preset temperature and a temperature of the storage chamber 26 received from the temperature sensor 23. Thus, the control unit 19 adjusts the "on" ratios of the heaters 17A and 17B to 17D so as to control heat generation thereof.

Figure 4:
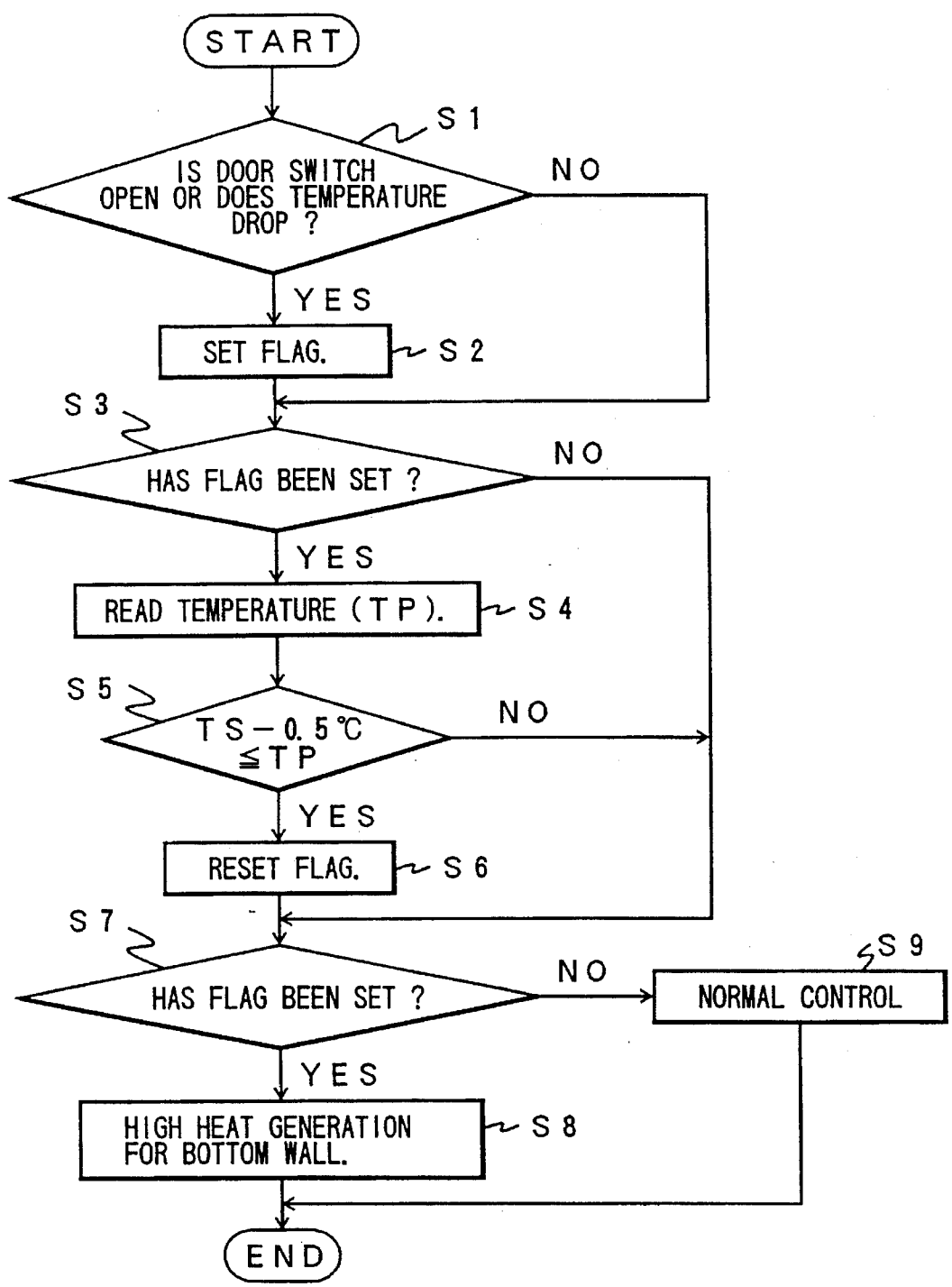
FIG. 4 is a flow chart showing a program of a control unit of the incubating cabinet.

Next, with reference to a flow chart of FIG. 4, the operation of the incubating cabinet 1 will be described. At step S1, the control unit 19 determines whether or not the heat resisting outer door 6 is open corresponding to the output of the door switch 2A or whether or not the temperature in the storage chamber 26 drops corresponding to the output of the temperature sensor 23. Unless the heat resisting outer door 6 is open or the temperature TP in the storage chamber 26 drops (because the heat resisting outer door 6 and the inner door 5 are open), the flow advances to step S3. At step S3, the control unit 19 determines whether or not a predetermined flag has been set. When the flag has not been set, the flow advances to step S7. Thereafter, the flow advances to step S9. At step S9, the control unit 19 performs normal control operation.

At step S9, the control unit 19 performs the above-described PID control for the heaters 17A to 17D with the same "on" ratio by the control switches 20 and 21. In addition, the control unit 19 operates the motor 12. Thus, air in the ceiling duct 13 and air in the side ducts 14, 14 are directed in the direction of arrow A of FIG. 2 by the cabinet circulation fan 11. The air flows horizontally in the ceiling duct 13 and then vertically in the side ducts 14, 14. Thus, the air flows from the air blow opening 16 to the storage chamber 26. On the other hand, air in the storage chamber 26 is directed in the direction of arrow B of FIG. 2 by the cabinet circulation fan 11. Thus, the air flows to the air intake opening 15 of the ceiling duct 13.

Since warm air flows upward, according to the present invention, the inside of the inner box 4, namely the inside of the storage chamber 26, can be equally heated without need to dispose a heater at an upper portion of the space 9. In addition, since the heaters 17A to 17C are disposed in contact with the inner box 4, when the heat insulating outer door 6 and the inner door 5 are opened and closed, even if the temperature in the inner box 4 abruptly drops, the temperature TP can be restored to the preset temperature TS in a shorter time than the conventional construction where the heaters are disposed on the heat insulating material 3. In addition, according to the present invention, the heat leak characteristic is improved.

The cabinet circulation fan 11 circulates air inside the storage chamber 26 in the directions of arrows A and B. In other words, air in the storage chamber 26 is sucked from the air intake opening 15. The air flows in the side ducts 14, 14 through the ceiling duct 13. The air is blown to the storage chamber 26 from the air flow openings 16, 16 of the side ducts 14, 14. Thus, air in the storage chamber 26 is equally agitated.

Thus, the storage chamber 26 is indirectly heated through the adjacent space 9. In addition, since the heaters 17A to 17D directly heat the corresponding wall surfaces of the inner box 4, the temperature in the storage chamber 26 can be kept equal. Moreover, the temperature restoration characteristic of the storage chamber 26 can be improved.

The air blow openings 16, 16 of the side ducts 14, 14 are disposed in the vicinity of the bottom portion of the storage chamber 26. The bottom heater 17A is disposed on the outer surface of the bottom wall 4A of the inner box 4. The humidifying tray 8 is disposed on the bottom wall 4A. The humidifying tray 8 is mainly heated by the bottom heater 17A. Thus, water W in the humidifying tray 8 is evaporated as steam. The steam is directed to the storage chamber 26 by the air blown from the air blowing opening 16. Thus, the inside of the storage chamber 26 is humidified at approximately 98% RH.

When the heat insulating outer door 6 is opened or the temperature TP in the storage chamber 28 drops (because the heat insulating outer door 5 and the inner door 5 are opened), the flow advances from step S1 to step S2. At step S2, the control unit 19 sets the flag. The reason that both the door switch 2A and the temperature sensor 23 are used is in that the temperature TP in the storage chamber 26 is proportional to the temperature around the incubating cabinet 1, the opening angle of the heat insulating outer door 6, and its opening time.

At step S3, the control unit 19 determines whether the flag has been set. Since the flag has been set, the control unit 19 reads the present temperature TP in the storage chamber 26 through the temperature sensor 23 at step S4. At step S5, the control unit 19 determines whether or not the temperature TP exceeds (preset temperature TS-0.5° C.). When the present temperature TP in the storage chamber 26 does not exceed this value, the control unit 19 determines whether or not the flag has been set at step S7. Since the flag has been set, the flow advances to step S8. At step S8, the control unit 19 performs the PID control for the switches 20 and 21 so that the "on" ratio of the bottom heater 17A is higher than the "on" ratios of the side heaters 17B, 17B, the rear heater 17, and the door heater 17D (namely, the heat generation of the bottom heater 17A is higher than that of the other heaters 17B, 17B, 17C, and 17D).

As described above, the bottom heater 17A is disposed in contact with the outer surface of the bottom wall 4A of the inner box 4 and the humidifying tray 8 is disposed on the bottom wall 4A. Thus, when the "on" ratio of the bottom heater 17A is higher than the "on" ratios of the other heaters 17B, 17B, 17C, and 17D, the heating temperature of the humidifying tray 8 can be raised. Consequently, until the temperature in the storage chamber 26 reaches the preset temperature TS, the water W evaporates from the humidifying tray 8 and thereby the storage chamber 26 is sufficiently humidified. Thus, even if the humidity quickly drops when the heat resisting outer door 6 and the inner door 5 are opened and closed, the humidity in the storage chamber 26 can be restored to the preset humidity (98% RH) in a short time.

Although the bottom heater 17A is controlled corresponding to the outer temperature and the opening degree of the heat insulating outer door 6, the control is finished in approximately 15 minutes. When the temperature TP in the storage chamber 26 exceeds (preset temperature TS-0.5°), the flow advances from step S5 to step S6. At step S6, the control unit 19 resets the flag. Thus, the control unit 19 restores the heaters 17A to 17D to the normal operation mode at step S9.

In the above-described embodiment, the heat amount of the bottom heater 17A is increased so as to improve the humidifying performance of the humidifying tray 8 on the bottom wall 4A. However, it should be noted that the heaters 17A to 17D may be separately controlled and temperature sensors may be disposed on the bottom wall 4A, the left and right side walls 4B, 4B, the rear wall 4C, and the heat insulating outer wall 6 so that the "on" ratio of one heater is higher than the "on" ratios of other heaters. In this construction, the temperature distribution in the storage chamber 26 becomes more stable, thereby precisely controlling the temperature.

In the above-described embodiment, the heaters 17A to 17C are disposed on the bottom wall 4A, the left and right side walls 4B, 4B, and the rear wall 4C, respectively. However, the heaters may be disposed only on the bottom wall 4A, and the left and right side walls 4B, 4B. Alternatively, a heater may be disposed on the ceiling wall 4A.

According to the present invention, a space is formed between the inner box and the heat insulating material. A heating unit is disposed in the space. Thus, the inner box can be equally heated through the space around the inner box. In particular, the heating unit is constructed of a plurality of heating means disposed on at least the bottom wall and the left and right side walls. The heating means are independently controlled by the control unit. Thus, when the humidifying tray is disposed in the storage chamber, it can be quickly humidified. In addition, the temperature control in the storage chamber can be more equally and precisely performed.

Moreover, since the heating unit is disposed in contact with the inner box, it can be directly heated. After the temperature in the inner box drops due to the opening of the outer door and the like, the preset temperature can be quickly restored. In addition, since the heating unit is disposed in the inner box, the amount of heat that leaks out from the outer box and so forth is reduced, thereby contributing to saving energy.

Although the present invention has been shown and described with respect to a best mode embodiment thereof, it should be understood by those skilled in the art that the foregoing and various other changes, omissions, and additions in the form and detail thereof may be made therein without departing from the spirit and scope of the present invention.

What is claimed is:

1. An incubator, comprising:

an outer box made from a heat insulating material and having an inner portion and an opening in one wall;

an inner box disposed in said outer box with a space between the inner portion of said outer box and said inner box, said inner box forming a chamber with an opening aligned with the opening of the outer box;

a heating unit disposed in said space for heating the inside of the inner box, said heating unit comprising a plurality of heating elements disposed at least on the outside of a bottom wall and left and right side walls of said inner box;

a door to open and close the opening to the interior of the inner box chamber;

a humidifying tray for holding a liquid disposed on the bottom wall of the inner box; and a control unit for independently controlling each of the heating elements to cause the heat output of the respective heating element for the inner box bottom wall to be higher than the heat output of the other heating elements after said door is opened and closed to evaporate the liquid in the humidifying tray to restore the humidity in the chamber and for causing all of said elements to restore the temperature in the chamber to a preset temperature.

* * * * *